United States Patent [19]
Fitzgerald

[11] Patent Number: 5,827,543
[45] Date of Patent: Oct. 27, 1998

[54] METHODS AND COMPOSITIONS FOR THE PREVENTION AND TREATMENT OF UROGENITAL DISORDERS

[75] Inventor: Jamesina Anne Fitzgerald, Hamilton, Ohio

[73] Assignee: The Procter & Gamble Company, Cincinnati, Ohio

[21] Appl. No.: 569,030

[22] Filed: Dec. 7, 1995

[51] Int. Cl.$^6$ .................................................. A61K 33/24
[52] U.S. Cl. .............................. 424/653; 514/29; 514/37; 514/39; 514/41; 514/154; 514/163; 514/192; 514/199; 514/200; 514/390; 514/398
[58] Field of Search .............................. 424/653; 514/29, 514/37, 39, 41, 154, 163, 192, 199, 200, 390, 398

[56] References Cited

U.S. PATENT DOCUMENTS

| | | | |
|---|---|---|---|
| 4,049,817 | 9/1977 | Laber et al. | 424/270 |
| 4,514,421 | 4/1985 | Herschler | 418/110 |
| 5,221,664 | 6/1993 | Berkowitz et al. | 514/6 |
| 5,256,684 | 10/1993 | Marshall | 514/398 |

FOREIGN PATENT DOCUMENTS

| | | | |
|---|---|---|---|
| 962163 | 6/1950 | France . | |
| 951910 | of 1965 | France . | |
| 63-174926 | 7/1988 | Japan | A61K 31/29 |
| WO 92/01457 | 2/1992 | WIPO | A61K 33/24 |
| WO 95/32720 | 12/1995 | WIPO | A61K 33/24 |

OTHER PUBLICATIONS

Abstract from France Patent (2978) filed Oct. 1963.
M. Windholz et al., *The Merek Index*, 10th Ed. p. 882 abstract No. 6033 (1983).
Cavier, R., "Etude des propriérés parasiticides de quelques complexes bismuthiques de l'oxy–8 quinoléine", Annales pharmaceutiques francaises, 1973, 31, No. 4, pp. 173–178 (translation attached).
Pitlik, S., et al., "Cryptosporidial Cholecystitis", The New England Journal of Medicine, vol. 308, No. 16 (Apr. 21, 1983), p. 967.
Than, U Pe, et al., "The Alkaloids of Holarrhena Antidysenterica", Union of Burma Journal of Science and Technology, vol. 2, Dec. 1969, pp. 423–436.
Willard, F. L., et al., "Survey of Chemical Compounds Tested In Vitro Against Rumen Protozoa for Possible Control of Bloat", vol. 15, No. 5, Sep. 1967, pp. 1014–1019.
DuPont, H., et al., Symptomatic Treatment of Diarrhea With Bismuth Subsalicylate Among Students Attending a Mexican University, Gastroenterology, vol. 73, (1977), pp. 715–718.
DuPont, H., "Enteropathogenic Organisms: New Etiologic Agents and Concepts of Disease", Medical Clinics of North America, vol. 62, No. 5 (1978), pp. 945–960.
Wolfe, M., "The Treatment of Intestinal Protozoan Infections", Medical Clinics of North America, vol. 56, No. 3 (1982), pp. 707–720.
Journal of the American Medical Association, "Travelers' Diarrhea", vol. 253, No. 18 (1985), pp. 2700–2704.
DuPont, L., "Nonfluid Therapy and Selected Chemoprophylaxis of Acute Diarrhea", The American Journal of Medicine, vol. 78, Suppl. 6B (1985), pp. 81–90.
Johnson, P., et al., "Comparison of Loperamide With Bismuth Subsalicylate for the Treatment of Acute Traveler's Diarrhea", The Journal Of the American Medical Association, vol. 255, No. 6 (1986), pp. 757–760.
Steffen, R., "Anerkannte Prinzipien zur Prophylaxe und Therapie der Reisediarrhoe", Schweiz. med. Wschr. 116, Nr. 20 (1986), pp. 670–673 (translation provided).
DuPont, H., et al., "Prevention of Travelers' Diarrhea By the Tablet Formulation of Bismuth Subsalicylate", The Journal of the American Medical Association, vol. 257, No. 10 (1987), pp. 1347–1350.
White, N., "Drug Treatment and Prevention of Malaria", European Journal of Clinical Pharmacology, vol. 34 (1988), pp. 1–14.
D'Alessandro, A., "Amebiasis Then", American Journal of Tropical Medicine and Hygiene, vol. 41, No. 3, Suppl. (1989), pp. 38–39.
Steffen, R., "Worldwide Efficacy of Bismuth Subsalicylate in the Treatment of Travelers' Diarrhea", Reviews of Infectious Diseases, vol. 12, Suppl. 1 (1990), pp. S80–S86.
Long, E., et al., "Alga Associated with Diarrhea in Patients with Acquired Immunodeficiency Syndrome and in Travelers", Journal of Clinical Microbiology, vol. 28, No. 6 (1990), pp. 1101–1104.
Wolfe, M., "Acute Diarrhea Associated With Travel", The American Journal of Medicine, vol. 88, Suppl. 6A (1990), pp. 34S–37S.
Qadri, S.M.H., "Infectious Dairrhea: Managing a Misery that is Still Worldwide", Postgraduate Medicine, vol. 88, No. 5 (1990), pp. 169–184).
Farthing, M.J.G., et al., "Treatment and Prevention of Travellers' Diarrhoea", Gastroenterology International, vol. 5, No. 3 (1992), pp. 162–175.
Zinsser Microbiology, 20th ed., Appleton & Lange (1992), pp. 1161–1173.
Arduino, R., et al., "Travellers' Diarrhoea", Bailliere's Clinical Gastroenterology, vol. 7, No. 2 (1993), pp. 365–385.
Chak, A., et al., "Traveler's Diarrhea", Gastroenterology Clinics of North America, vol. 22, No. 3 (1993), pp. 549–561.

(List continued on next page.)

*Primary Examiner*—Kevin E. Weddington
*Attorney, Agent, or Firm*—Mary Catherine Poland; Douglas C. Mohl; Jacobus C. Rasser

[57] ABSTRACT

The subject invention encompasses methods for prevention and treatment of a human or lower animal subject having a urogenital disorder caused or mediated by one or more parasitic protozoa comprising administering to the subject bismuth and one or more antimicrobials. The subject invention also encompasses compositions comprising bismuth and one or more antimicrobials for the prevention and treatment of a human or lower animal subject having a urogenital disorder caused or mediated by one or more parasitic protozoa.

16 Claims, No Drawings

OTHER PUBLICATIONS

American Health Consultants, "Cryptosporidiosis in Milwaukee", vol. 12, No. 15 (1993), pp. 113–115.

Wittner, M., et al., "Parasitic Infections in AIDS Patients: Cryptosporidiosis, Isosporiasis, Microsporidiosis, Cyclosporiasis", Infectious Disease Clinics of North America, vol. 7, No. 3 (1993), pp. 569–586.

Weber, R., et al., "Disseminated Microsporidiosis Due to *Encephalitozoon Hellem*: Pulmonary Colonization, Microhematuria, and Mild Conjunctivitis in a Patient with AIDS", Clinical Infectious Diseases, vol. 17 (1993), pp. 415–419.

Kuhls, T., "Protozoal Infections of the Intestinal Tract in Children", Advances in Pediatric Diseases, vol. 8 (1993), pp. 177–202.

Scott, D., et al., "Treatment of Gastrointestinal Infections", Bailliere's Clinical Gastroenterology, vol. 7, No. 2 (1993), pp. 477–499.

Martindale, The Extra Pharmacopoeia, "Gastro–intestinal Agents", Thirtieth Ed., The Pharmaceutical Press (1993), p. 872.

Health, "Are Milwaukee–Type Parasites Floating in My Drinking Water?" (1993), p. 14.

Sun, T., et al., "Intestinal Microsporidiosis: Report of Five Cases", Annals of Clinical and Laboratory Science, vol. 24, No. 6 (1994), pp. 521–532.

American Drug Index, 38th Ed. (1994), pp. 568–569.

Upcroft, P., "Multiple Drug Resistance in the Pathogenic Protozoa", Acta Tropica, vol. 56 (1994), pp. 195–212.

Herwaldt, B., et al., "Infections with Intestinal Parasites in Peace Corps Volunteers in Guatemala", Journal of Clinical Microbiology (1994), pp. 1376–1378.

Physicians' Desk Reference, 48th Ed. (1994), pp. 724–726.

Jernigan, et al., "Parasitic Infections of the Small Intestine", Gut, vol. 35, No. 3 (1994), pp. 289–293.

Fritsche, T., et al., "Introduction to Diagnostic Parasitology: Biologic, Clinical, and Laboratory Considerations", Manual of Clinical Microbiology, Sixth Ed., ASM Press (1995), pp. 1141–1144.

Chevalier, C., et al., "Bilan Des Antiparasitaires A Usage Veterinaire: Antihelminthiques, Anticoccidiens, Antifongiques, Ectoparasiticides" (translation attached), Laboratory of Therapeutic Chemistry, College of Pharmacy, 37042 Tours Cedex, pp. 624–630.

METHODS AND COMPOSITIONS FOR THE PREVENTION AND TREATMENT OF UROGENITAL DISORDERS

BACKGROUND OF THE INVENTION

While many industrialized countries have come to regard parasitic infection as a problem of impoverished developing countries, this is far from the truth. The incidence of parasitic infection, especially of the urogenital tract, continues to present a serious health concern. For example, in the United States in some areas, the incidence of urogenital infection due to *Trichomonas vaginalis* is reported to be as high as fifty percent with twenty to fifty percent of infected women and ninety percent of infected men being asymptomatic. *Zinsser Microbiology*, 20th Edition, 1173, (1992). Additionally, in the case of urogenital infection, incidence of infection is notoriously underestimated due to physicians prescribing broad spectrum antibiotics rather than isolating the offending, fastidious pathogen and the failure of physicians to report sexually transmitted vaginal diseases. Traditional treatment regimens for such infections consist of administration of a selective action antibiotic. However, antimicrobial resistance to such drugs raises concern about the ability to effectively treat parasitic infections in the future. Therefore, the need for effective anti-parasitic treatment therapies continues to grow.

It has been discovered by the present invention that the administration of bismuth salts and one or more antimicrobials may be effective for the prevention and/or treatment of urogenital disorders caused or mediated by parasitic protozoa. Thus, an object of the present invention is to provide safe and effective compositions and methods for preventing and/or treating urogenital disorders caused or mediated by parasitic protozoa. A further object of the invention is to provide such a method comprising the administration of bismuth and one or more antimicrobials.

These and other objects of the present invention will become readily apparent from the detailed description which follows.

SUMMARY OF THE INVENTION

The present invention relates to a method for treatment of a human or lower animal subject having a urogenital disorder caused or mediated by one or more parasitic protozoa comprising administering to the subject from about 50 milligrams to about 10,000 milligrams of bismuth, per day, for from about 1 to 56 days; and from about 100 milligrams to about 10,000 milligrams of each of one or more antimicrobials, per day, for from about 1 to about 21 days.

The present invention also relates to a method of prevention in a human or lower animal for a urogenital disorder caused or mediated by one or more parasitic protozoa comprising administering to the subject from about 50 milligrams to about 10,000 milligrams of bismuth, per day, for from about 1 to 21 days; and from about 100 milligrams to about 10,000 milligrams of each of one or more antimicrobials, per day, for from about 1 to about 14 days.

DETAILED DESCRIPTION OF THE INVENTION

The methods of the present invention comprise the prevention and/or treatment of urogenital disorders caused or mediated by one or more parasitic protozoa. Such urogenital disorders are prevented and/or treated by the administration of bismuth and one or more antimicrobials. The components of the present invention are more fully defined below.

Urogenital Disorder

The term "urogenital disorder", as used herein, encompasses any infection, disease or other disorder of the urinary and/or reproductive systems, caused or mediated by one or more parasitic protozoa. Such disorders include one or more of the following conditions: vaginitis; vaginal burning, itching, discharge; ulcerative lesions; dysuria; painful urination; prostatitis; urethritis; epidiymitis; urethral stricture; and any other urogenital condition commonly associated with infection by parasitic protozoa.

In immunocompromised subjects, urogenital disorders caused or mediated by parasitic protozoa may be more severe and life threatening than the common disorders listed above. Therefore, the term "urogenital disorder" also includes any condition commonly associated with protozoa infection in immunocompromised subjects including but not limited to foul smelling discharge, bleeding or purulent urogenital lesions, severe pruritus, painful dysuria, and microhematuria.

Parasitic Protozoa

Protozoa are unicellular, eucaryotic organisms which contain a nucleus, or nuclei, and cytoplasm. The term "parasitic protozoa", as used herein, refers to Protozoa such as *Trichomonas vaginalis*, and the microsporidia of the genera Pleistophora, Nosema, and Encephalitozoon. Preferred parasitic protozoa are *Trichomonas vaginalis, Encephalitozoon hellem,* and combinations thereof. Most preferred parasitic protozoa is *Trichomonas vaginalis*. The organisms are fully described in *Manual of Clinical Microbiology*, Sixth Edition, 1204–1205, 1213–1217, and 1225–1228 (1995), which is incorporated herein by reference.

Diagnosis of urogenital disorders caused or mediated by parasitic protozoa may be accomplished by any method commonly used in the medical community. Such methods are fully described in *Manual of Clinical Microbiology*, as referenced above.

Bismuth

The methods of treatment and/or prevention in the present invention involve administration of bismuth. As used herein, the quantity of bismuth is by weight of elemental bismuth.

The preferred duration of bismuth administration will vary according to the specific urogenital disorder to be treated and the physical condition of the subject being treated. In general, as a method of treatment, bismuth may be administered in an amount of from about 50 milligrams to about 10,000 milligrams, and preferably from about 50 milligrams to about 5000 milligrams, per day, for from about 1 to about 56 days, preferably for from about 2 to about 28 days, and most preferably for from about 7 to about 21 days.

In general, as a method of prevention, bismuth may be administered in an amount of from about 50 milligrams to about 10,000 milligrams, and preferably from about 50 milligrams to about 5000 milligrams, per day, for from about 1 to about 21 days, and preferably for from about 1 to about 14 days. In a method of prevention, bismuth may be administered prior to potential exposure to parasitic protozoa. Such administration of bismuth may vary depending on the likelihood of parasitic protozoa exposure and condition of the subject and may be commenced at any time deemed beneficial by the medical community including from about 1 to about 7 days, from about 2 to about 5 days, and from about 3 to about 4 days, prior to potential exposure.

In the present methods, the term "bismuth", as used herein, includes bismuth in the form of a pharmaceutically-acceptable salt, bismuth or bismuth salt in the form of an organic or other complex which contains bismuth as an active ingredient, and mixtures thereof. Such organic complexes include 2,2'-spirobi[1,,32-benzodoxabismole]. Preferably, bismuth is administered in the present methods as a pharmaceutically-acceptable salt. Such bismuth salts include bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof. Bismuth citrate, bismuth subcitrate, tripotassium dicitrato bismuthate, bismuth tartrate, bismuth subsalicylate, and mixtures thereof are preferred bismuth salts for use in this invention.

The bismuth useful herein may be administered alone, or in combination with other pharmaceutically-acceptable components in a bismuth-containing composition. A variety of such compositions containing bismuth salts are commercially available. Such compositions include DeNol, containing tripotassium dicitrato bismuthate (by Brocades); Bislumina, containing bismuth aluminate (by Mazuelos); Roter, containing bismuth subnitrate (by Roterpharma); Devrom®, containing bismuth subgalate (by The Parthenon Co., Inc.); and Pepto-Bismol®, containing bismuth subsalicylate (by The Procter & Gamble Company).

Bismuth may be administered in the form of a douche, douche powder, suppository, tablet, ointment, cream, gel, mousse, foam or any other form which would administer bismuth intravaginally to the subject. The delivery systems are described in detail in *Remington's Pharmaceutical Sciences,* 18th Edition, 1609–1614, 1632, 1525, 1519–1544, 1597–1614, 1633–1675, (1990); and Ansel, et al., *Pharmaceutical Dosage Forms and Drug Delivery Systems,* Fifth Edition, 373–389, (1990).

Antimicrobial

The present invention also include administration of a safe and effective amount of one or more antimicrobials, per day. As used herein, the term "antimicrobial(s)" refers to one or more antimicrobials.

Typically, according to the present methods for prevention and treatment, each of the one or more antimicrobials is administered at a level of from about 100 milligrams to about 10,000 milligrams, per day, for from about 1 to about 28 days. Preferably, each of the one or more antimicrobials is administered at a level of from about 100 milligrams to about 8000 milligrams per day, and more preferably at from about 100 milligrams to about 5000 milligrams per day. It is also preferred that each of the antimicrobials is administered for from about 1 to about 7 to 10 days, more preferably for from about 1 to about 14 days, and most preferably for from about 1 to about 21 days. In the methods for prevention, it is further preferred that each of the one or more antimicrobials is administered for from about 1 to about 14 days, and preferably for from about 1 to about 7 to 10 days.

The specific dosage of antimicrobial(s) to be administered, as well as the duration of antimicrobial(s) treatment, are mutually dependent, and will also depend upon such factors as the specific antimicrobial used, the number of antimicrobials used in the treatment, the resistance pattern of the infecting organism to the antimicrobial used, the ability of the antimicrobial to reach minimum inhibitory concentrations at the site of the infection, the nature and extent of other infections (if any), the personal attributes of the subject, compliance with the treatment regimen, and the presence and severity of any side effects of the treatment. Therefore, in the case of prevention or treatment with more than one antimicrobial, the duration of administration should depend on the type of antimicrobial rather than the administration of the antimicrobials for the same number of days.

A wide variety of antimicrobials are useful in this invention. As used herein, the term "antimicrobial" refers to any naturally-occurring, synthetic or semi-synthetic compound or composition or mixture thereof, which is safe for human use as used in the methods of this invention, and is effective in killing or substantially inhibiting the parasitic protozoa when used in the methods of this invention. Antiprotozoal agents, antiparasitic agents and antibiotics are among the preferred antimicrobials useful herein.

Antiprotozoal and antiparasitic agents suitable for use in the present invention include any of the agents recognized in the medical community as acceptable for treating protozoal infection. Such antiprotozoal and antiparasitic agents include atovaquone, chloroquine phosphate, quinacrine hydrochloride, iodoquinol, pyrimethamine, and mefloquine hydrochloride.

Antibiotics can be generally classified by chemical composition into the following principal groups: the aminoglycosides, such as gentamicin, neomycin, kanamycin, and streptomycin; the macrolides, such as erythromycin, clindamycin, and rifampin; the penicillins, such as penicillin G, penicillin V, ampicillin and amoxycillin; the polypeptides such as bacitracin and polymyxin; the tetracyclines such as tetracycline, chlortetracycline, oxytetracycline and doxycycline; the cephalosporins such as cephalexin and cephalothin; quinolones such as ciprofloxacin, norfloxacin and ofloxacin; and such miscellaneous antibiotics as trimethoprim, sulfamethoxazole and the combination thereof, and chloramphenicol. These antibiotics can generally be said to function in one of four ways: inhibition of cell wall synthesis, alteration of cell wall permeability, inhibition of protein synthesis or inhibition of nucleic acid synthesis.

Other antimicrobials useful herein include the sulfonamides; nitrofurans, such nitrofurazon, nitrofurantoin, and furozolidone; metronidazole, tinidazole, and nimorazole. Antimicrobials among those useful herein are described in *Remington's Pharmaceutical Sciences,* 18th Edition, pp. 1173–1232 (1990), which is incorporated herein by reference.

While any of these antimicrobials may be used, penicillin, tetracycline, metronidazole, doxycycline, tinidazole, amoxycillin, ampicillin, nitrofurantoin, and atovaquone are among the preferred antimicrobials for use in the present invention.

As stated above, the specific preferred quantity of antimicrobial and duration of treatment used in the methods of this invention will, in addition to other factors, depend upon the particular antimicrobial used and its pharmacology. In general, though, the tetracyclines are preferably administered at a level of from about 100 milligrams to about 2,000 milligrams per day. Macrolides (such as erythromycin) are preferably administered at a level of from about 1,000 milligrams to about 4,000 milligrams per day. Penicillins are preferably administered at a level of from about 500 milligrams to about 3,000 milligrams per day. The aminoglycosides (such as neomycin) are preferably administered at a level of from about 100 milligrams to about 8,000 milligrams per day. Nitrofurans (such as nitrofurantoin) are administered preferably at levels of from about 100 milligrams to about 800 milligrams per day. Preferably, metronidazole is administered at a level of from about 375 or 500 to about 2,000 milligrams per day. Preferably, atovaquone is administered at a level of from about 750 to about 2250 milligrams, per day.

The specific method of administering the antimicrobial, according to the processes of this invention, may depend upon such factors as the particular antimicrobial(s) used, the site of infection, the amount of antimicrobial(s) to be administered per day, the presence of any adverse side effects, and the interactions (if any) between the antimicrobial(s) and the bismuth. Thus, the antimicrobial(s) may be administered under the process of this invention by single daily doses, or by administration in two, three, four, or more doses per day.

Bismuth/Antimicrobial Compositions

The present invention also provides compositions for the treatment of urogenital disorders comprising a safe and effective amount of bismuth and a safe and effective amount of one or more antimicrobials. Typically, these compositions comprise a safe and effective amount one or more antimicrobials; a safe and effective amount of bismuth; and pharmaceutically-acceptable carrier materials; wherein the safe and effective amount of the one or more antimicrobials and the bismuth is effective for preventing and/or treating a urogenital disorder caused or mediated by one or more parasitic protozoa.

A preferred composition comprises:
(a) from about 50 milligrams to about 5,000 milligrams of bismuth; and
(b) from about 100 milligrams to about 10,000 milligrams of each of one or more antimicrobials.

Preferably, the bismuth salt is present at a level of from about 50 milligrams to about 2500 milligrams. Also, preferably each of the one or more antimicrobials is present at a level of from about 100 milligrams to about 8000 milligrams.

The compositions of the present invention may contain optional components which affect the physical and therapeutic characteristics of the present compositions. In particular, a variety of pharmaceutically-acceptable carriers and excipients may be included, depending upon the particular intravaginal dosage form to be used. Suppositories, and tablets can be compressed, coated or multiple compressed, containing suitable binders, lubricants, diluents, disintegrating agents, coloring agents, flow-inducing agents and melting agents. Liquid intravaginal dosage forms include aqueous solutions, emulsions, suspensions, solutions, and/or suspensions reconstituted from granules or powders containing suitable solvents, preservatives, emulsifying agents, suspending agents, diluents, melting agents, and coloring agents.

Techniques and compositions for making intravaginal dosage forms useful herein are more fully described in the following references, all incorporated by reference herein: *Remington's Pharmaceutical Sciences,* 18th Edition, 1609–1614, 1632, 1525, 1519–1544, 1597–1614, 1633–1675, (1990); and Ansel, et al., *Pharmaceutical Dosage Forms and Drug Delivery Systems,* Fifth Edition, 373–389 (1990).

The compositions of this invention may be used according to the methods of this invention by administering the composition from 1 to 7 times per day, and preferably from 1 to 4 times per day; for from 1 to 21 days, preferably for from about 1 to about 14 days. The specific frequency of administration will depend upon such factors as the specific bismuth compound or composition and antimicrobial(s) used, the levels at which the components are incorporated in the composition, the nature and severity of the condition to be treated, and the nature of any concurrent therapy, if any.

Administration

The present invention comprises methods wherein the administration of bismuth and the administration of one or more antimicrobials are performed simultaneously (beginning and ending on the same day), concurrently (overlapping), or consecutively (sequential, but wherein the course of the treatment is substantially continuous). Preferably, the step of administering the antimicrobial(s) is not commenced prior to commencing the step of administering bismuth.

As used herein, the term "administering" refers to any method which, in sound medical practice delivers the compounds or compositions used in this invention to the subject to be treated in such a manner so as to be effective in the treatment of the urogenital disorder. Preferably, the bismuth is administered intravaginally in the form of a douche. The antimicrobial(s) is administered either orally, intravenously, intravaginally or any other method which effects systemic distribution, or local distribution to the site of the urogenital disorder, of the antimicrobial(s) in the subject. Oral ingestion of the antimicrobial(s) is a preferred method of administering the antimicrobial(s) in the methods of this invention.

The following non-limiting examples illustrate the methods and uses of the present invention.

EXAMPLE I

A young, college coed visits a campus health center for her routine annual gynecological exam, complaining of vaginal irritation. Upon examination of the vagina, the physician observes the presence of a foamy, yellowish-green discharge and chafing of the vagina, vulva, and perineum. Using a vaginal speculum, exudate is collected from the vaginal canal and a wet mount preparation is made promptly and analyzed microscopically. The presence of organisms, 5–20 m in length with a jerky-type motion confirms the presence of *Trichomonas vaginalis.* The patient is treated by a method of the present invention. A composition containing bismuth subsalicylate is administered in a liquid douche delivering approximately 2500 mg of bismuth per liter of douching solution, twice daily (a total of 5000 milligrams of bismuth daily) for twenty-one days. Atovaquone tablets (750 milligrams per tablet) are concurrently administered three times a day for 21 days, delivering a total of 2250 milligrams of atovaquone per day. Thereafter, vaginal samples from the patient are analyzed again, finding no trace of parasitic infection. The subject remains asymptomatic, and another vaginal analysis performed 5 months later is normal.

In the above example, tripotassium dicitrato bismuthate, bismuth tartrate, bismuth citrate, and bismuth subgallate, bismuth subnitrate may be substituted, respectively, for bismuth subsalicylate, with substantially similar results. Similarly, penicillin erythromycin, metronidazole, doxycycline, tinidazole, amoxicillin, ampicillin, nitrofurantoin, chloroquine phosphate, quinacrine hydrochloride, iodoquinol, pyrimethamine, and mefloquine hydrochloride may be substituted for atovaquone with substantially similar results.

EXAMPLE II

A male AIDS patient, who recently recovered from cryptosporidal diarrhea, reports symptoms of genital irritation to his primary healthcare provider. Upon examination of the patient's penis, a small, purulent lesion is observed one centimeter from the urethral opening. A thin smear of the exudate is prepared and stained for 90 minutes with Modified Trichome-Blue Stain before oil immersion examination, while a midstream urine sample is collected, centrifuged, and examined promptly via light microscopy. The results show no indication of urinary infection; however, the presence of spores with coiled polar tubules confirms an infection with *Encephalitozoon hellem.* The infection is treated by cleansing the lesion gently with non-medicated soap and topically applying a small amount of an ointment consisting of 10% bismuth subcitrate, 0.75% metronidazole, and 0.1% iodoquinol twice daily over the lesion for about 28 days, until the lesion has healed completely. Thereafter, visual inspection of the penis is performed, finding slight scarring but no trace of parasitic infection.

In the above example, bismuth citrate, bismuth tartrate, bismuth aluminate, bismuth subgallate, and bismuth subsalicylate are substituted, respectively, for bismuth subcitrate, with substantially similar results. Similarly, penicillin, erythromycin, doxycycline, tinidazole, amoxicillin, ampicillin, nitrofurantoin, and atovaquone are substituted, respectively, for metronidazole or iodoquinol, with substantially similar results. In addition, either antibiotic can be eliminated from the regimen (e.g. due to hypersensitivity) and maintain therapeutic efficacy.

EXAMPLE III

A young man, in the presence of his physician, confides to his future bride two days before their marriage that he is being treated for a urethral infection caused by *Trichomonas vaginalis*, reportedly from using a contaminated towel at his gym. The physician advises the groom to continue his current therapy until eradication of the parasite is complete. Clinical analyses indicate that the bride currently is not infected. Since the use of condoms is not considered due to religious beliefs, the bride is given 3500 milligrams of bismuth, administered as bismuth subnitrite in a vaginal suppository, for use thirty minutes before sexual intercourse. Following intercourse, a douche is administered delivering 500 milligrams of furolzolidone in one liter of douching solution. The suppository and douching regimen are used for about 30 days or until her husband is determined to be free of infection. At this time, vaginal samples are taken from the wife and analyzed and no evidence of parasitic infection is found.

What is claimed is:

1. A method for treatment of a human or lower animal subject having a urogenital disorder caused or mediated by one or more parasitic protozoa comprising administering to the subject from about 50 milligrams to about 10,000 milligrams of bismuth, per day for from about 1 to 56 days; and from about 100 milligrams to about 10,000 milligrams of each of one or more antimicrobials, per day, for from about 1 to about 28 days.

2. The method of claim 1 wherein the bismuth is administered intravaginally in the form of a suppository at a level of from about 50 milligrams to about 5000 milligrams, per day.

3. The method of claim 2 wherein the bismuth is selected from the group consisting of bismuth aluminate, bismuth subcarbonate, bismuth subcitrate, bismuth citrate, tripotassium dicitrato bismuthate, bismuth subgalate, bismuth subsalicylate, bismuth tartrate, and mixtures thereof.

4. The method of claim 1 wherein each of the one or more antimicrobials is administered orally at a level of from about 100 milligrams to about 8000 milligrams, per day.

5. The method of claim 4 wherein the one or more antimicrobials are selected from the group consisting of penicillin, tetracycline, metronidazole, doxycycline, tinidazole, amoxycillin, ampicillin, nitrofurantoin, and atovaquone.

6. The method of claim 1 wherein the bismuth is administered intravaginally in the form of a douche for from about 2 to 28 days and the one or more antimicrobials are administered in the form of a tablet for from about 1 to about 21 days.

7. The method of claim 1 wherein the parasitic protozoa are selected from the group consisting of *Trichomonas vaginalis, Encephaliztozoon hellem*, and combinations thereof.

8. A method for prevention in a human or lower animal subject in need thereof, of a urogenital disorder caused or mediated by one or more parasitic protozoa comprising administering to the subject from about 50 milligrams to about 10,000 milligrams of bismuth, per day, for from about 1 to about 21 days; and from about 100 milligrams to about 10,000 milligrams of each of one or more antimicrobials, per day, for from about 1 to about 14 days.

9. The method of claim 8 wherein the bismuth is administered intravaginally in the form of a douche at a level of from about 50 milligrams to about 5000 milligrams, per day.

10. The method of claim 9 wherein the bismuth is selected from the group consisting of bismuth aluminate, bismuth subcarbonate, bismuth subcitrate, bismuth citrate, tripotassium dicitrato bismuthate, bismuth subgalate, bismuth subsalicylate, bismuth tartrate, and mixtures thereof.

11. The method of claim 8 wherein each of the one or more antimicrobials is administered orally at a level of from about 100 milligrams to about 8000 milligrams, per day.

12. The method of claim 11 wherein the one or more antimicrobials are selected from the group consisting of penicillin, tetracycline, metronidazole, doxycycline, tinidazole, amoxycillin, ampicillin, nitrofurantoin, and atovaquone.

13. The method of claim 8 wherein the bismuth is administered for from about 1 to about 14 days and the one or more antimicrobials are administered for from about 1 to about 7 to 10 days.

14. The method of claim 8 wherein the parasitic protozoa are selected from the group consisting of *Trichomonas vaginalis, Encephalitozoon hellem*, and combinations thereof.

15. The method of claim 1 wherein the subject is administered a composition comprising:
   (a) a safe and effective amount of bismuth;
   (b) a safe and effective amount of one or more antimicrobials;
   (c) pharmaceutically-acceptable carriers materials; and
wherein the safe and effective amount of the bismuth and one or more antimicrobials is effective for treating the urogenital disorder caused or mediated by one or more parasitic protozoa.

16. The method of claim 8 wherein the subject is administered a composition comprising:
   a) a safe and effective amount of bismuth;
   (b) a safe and effective amount of one or more antimicrobials;
   (c) pharmaceutically-acceptable carriers materials; and
wherein the safe and effective amount of the bismuth and one or more antimicrobials is effective for preventing the urogenital disorder caused or mediated by one or more parasitic protozoa.

* * * * *